United States Patent
Giambruno

(12) 
(10) Patent No.: US 6,669,726 B2
(45) Date of Patent: Dec. 30, 2003

(54) ORTHOTOPIC TOTAL ARTIFICIAL HEART

(76) Inventor: Juan M. Giambruno, Av Brasil 3079, Ap. 502, C.P. 11300, Montevideo (UY)

( * ) Notice: Subject to any disclaimer, the term of this patent is extended or adjusted under 35 U.S.C. 154(b) by 0 days.

(21) Appl. No.: 09/497,683

(22) Filed: Feb. 4, 2000

(65) Prior Publication Data

US 2003/0191529 A1 Oct. 9, 2003

(30) Foreign Application Priority Data

Aug. 3, 1999 (UY) ................................................. 25640
Dec. 14, 1999 (UY) ................................................. 02852

(51) Int. Cl.[7] .............................................. A61M 1/10
(52) U.S. Cl. ..................................... 623/3.17; 623/3.16
(58) Field of Search ............................... 623/3.17, 3.16, 623/3.18, 3.19, 3.2, 3.21, 3.22, 3.23, 3.24, 3.25; 600/16

(56) References Cited

U.S. PATENT DOCUMENTS

| | | | |
|---|---|---|---|
| 4,851,002 A | * 7/1989 | Slonina | 623/3 |
| 4,863,461 A | * 9/1989 | Jarvik | 623/3 |
| 4,902,291 A | 2/1990 | Kolff | |
| 5,006,104 A | 4/1991 | Smith et al. | |
| 5,089,020 A | 2/1992 | Koppert | |
| 5,139,517 A | * 8/1992 | Corral | 623/3 |
| 5,306,295 A | 4/1994 | Kolff et al. | |
| 5,423,886 A | 6/1995 | Arru et al. | |
| 5,569,156 A | 10/1996 | Mussivand | |
| 5,674,281 A | 10/1997 | Snyder | |
| 5,704,891 A | 1/1998 | Mussivand | |
| 5,751,125 A | 5/1998 | Weiss | |
| 5,879,375 A | 3/1999 | Larson, Jr. et al. | |

OTHER PUBLICATIONS

Bethesda Conference Report—Walter E. Pae, Jr, MD, Conference Chairman—Ann Thorac Surg 1998;66:1452–65.
Clinical Experience with 111 Thoratec Ventricular Assist Devices—Lawrence r. McBride, MD, Keith S. Naunheim, MD, Andrew C. Fiore, MD, Debbie A. Moroney, BSN, and Marc T. Swartz, BA—Ann Thorac Surg 1998;67:1233–9.
Development of an Electrohydraulic Total artificial Heart at the National Cardiovascular Center, Osaka, Japan—Toru Masuzawa, et al.—M249—M253.
Progress in the Development of the ABIOMED Total Artificial Heart—Robert T. V. Kung, et al.—M245—M248.
Anatomic Fitting Studies of a Total Artificial Heart in Heart Transplant Recipients—Kiyotaka Fukamachi, et al. M337—M342.
Mechanical and Biological Support—Sanjay M. Mehta, MD, et al.—585—593.
Official Organs 23(8) 741—746, Blackwell Science, Inc.—1999 International Society for Artificial Organs Wada et al.
Official Organs 23(3) 242—248, Blackwell Science, Inc.—1999 International Society for Artificial Organs Tatsumi et al.
Official Organs 23(3) 229—234, Blackwell Science, Inc.—1999 International Society for Artificial Organs Zhang et al.
Official Organs 23(3) 221—228, Blackwell Science, Inc.—1999 International Society for Artificial Organs Abe et al.

(List continued on next page.)

*Primary Examiner*—Bruce Snow

(57) ABSTRACT

An orthotopic total artificial heart for replacing the human heart comprising a new design of two assembled blood chambers with an original layout between themselves and between their inlet and outlet ports. Such design enables a significantly better space utilization inside the anterior mediastinum than the prior art; realizing the required anatomical fit.

4 Claims, 24 Drawing Sheets

OTHER PUBLICATIONS

Official Organs 17(12) 1022—1035, Blackwell Science, Inc.—1999 International Society for Artificial Organs Chatel et al.

Perfusion 1990: 5: 181—191 Biomedical engineering management of Novacor left ventricular assist system (LVAS) patients—John M. Pristas, et al.

Official Organs 16(4) 398—406, Blackwell Science, Inc.—1999 International Society for Artificial Organs Takatani et al.

Implantation Technique for the Cardio West Total Artificial Heart—Francisco A. Arabia, MD, et al.– 698—704.

Bridge to Transplant with the Novacor Left Ventricular Assist System—Robert C. Robbins, MD, et al.—695—697.

Digital Signal Processor for Ventricular Assist System—Eisuke Tatsumi, et al.—M619—M625.

Progress of an Electrohydraulic Total Artificial Heart System with a Separate Energy Converter—Toru Masuzawa, et al. —471—477.

Thoughts and Progress vol. 21, No. 8. 1997—Won Gon Kim, et al.—957—960.

Dynamic In Vitro and In Vivo Performance of a Permanent Total Artificial Heart—Gerson Rosenberg, et al.—87—94.

Artificial Organs 21(11):1211—1216, Blackwell Science, Inc. 1997 International society for Artificial Organs—Kou Imachi.

Artificial Organs 21(10):1098—1104, Blackwell Science, Inc. 1997 International society for Artificial Organs—Kou Imachi.

* cited by examiner

ORTHOTOPIC TOTAL ARTIFICIAL HEART

FIELD OF THE INVENTION

This invention pertains to medical prostheses, and in particular, to an artificial heart. In particular, it is conceived to satisfy the current need for creating a new and original design to achieve a Total Artificial Heart in order to replace a native sick heart in its terminal stage or as a bridge to cardiac transplantation or to be used after a heart transplantation failure.

BACKGROUND OF THE INVENTION

At present, when there is a patient with a serious heart disease, which for different reasons is nonreversible, cardiac transplantation is considered as the solution, provided that the patient gets a donor. However, in the United States, for example, there are about 60,000 patients per year under this situation and only about 6% to 10% get a transplantation due to the current difficulties to find an adequate heart donor.

A Total Artificial Heart (TAH) is recognized as a progress in case of such an extreme situation of a cardiac failure. The present generation of this kind of devices includes the use of different models. In addition, there are partial circulatory assistance devices in use, generally called Left Ventricular Assistance Systems (LVAS).

Under extreme haemodynamic failure circumstances, these devices are used at present as a bridge to transplantation. They permit to keep the patient alive while the patient awaits for the appropriate donor, preventing a serious systemic damage caused by the progressive deterioration of the haemodynamia, which can later compromise the viability of other organs if the patient gets a transplantation.

However, the present Total Artificial Heart generation has had problems. Even though these devices have kept patients alive under extreme circumstances, they have not been able to provide them with an acceptable quality of life.

Most important, due to the disagreement between the sizes of the current generation devices and the space inside the mediastinum available for the current models, i.e. the so called lack of anatomical fit, many of these devices do not place the artificial ventricular and other elements necessary for their operation in an orthotopic position. Several elements are placed outside the body and coupling of parts located both inside and outside of the human body is made through the skin. Several pathological phenomena occur, such as local infections that are later transformed into more serious infections, ascendent infections, skin ulcerations and countless problems for the patient and his/her quality of life. An example of their limitations is the need for the patient to be connected to a pneumatic console. In addition, by placing these parts outside the chest, risks and problems are increased during operation; it also causes surgical complications and problems during the postoperative period such as bleeding, hematomas, infection, and compressions.

Furthermore, due to the reduced space available within the chest, some of the devices of the present generation do not have an adequate size to produce a good final diastolic volume. Hence, often times, in order to obtain an adequate blood flow rate, these devices resort to a significant increase of the heart frequency which causes additional turbulence as a result of and increase in the the blood flow linear velocity. This situation can be the cause of more serious haematological complications, such as haemolysis and bleeding and cause a faster deterioration of the materials that form these devices. On these grounds, a better utilization of the space available inside the mediastinum to achieve a significant increase on the diastolic volume would be highly desirable.

Another type of haematological complications associated with devices of the present generation as thrombosis and embolisms. In some of these devices the internal walls of the cavities through which blood circulates have areas with stasis, corners or boundaries between the different materials of their surfaces and with stitches between them, all of which created a very high embolism risk.

The aforementioned artificial devices present haemostatic complications such as bleeding, occurring because the blood has to go through long circuits of rigid prosthetic tubes with many stitches at each end. These artificial prosthetic tubes do not respond to a need to increase the blood flow rate like native vessels do in reflex mode, i.e. by greatly increasing their diameter. This deficiency causes a larger increase in blood pressure which further stresses the above mentioned stitches and causes the present generation Total Artificial Hearts to operate under more stringent conditions.

Another important problem of these devices is their limitation to compensate the different blood volumes physiologically handled by the pulmonary circuit and the systemic circuit. To alleviate this situation, the surgeon has to create a communication between the two circuits during the implantation surgical procedure, usually making an interauricular communication. However, the size of the surgical opening, in particular and the efficacy of this procedure in general, is often questioned because of frequently occurring systemic or pulmonary hemodynamic congestions.

Accordingly, there remains a need for an artificial heart without the attendant disadvantages of conventionally available artificial hearts.

SUMMARY OF THE INVENTION

In general, the present invention comprises an artificial heart that may be implanted in orthotopic position in a circulatory system of a living being, e.g., mammals, that preferrably and anatomically fits within a mediastinum space created by removing at least the two native ventricles, said artificial heart comprising:

one right blood chamber, said right blood chamber having an elongated shape essentially directed up and back, said right blood chamber having one right inlet port for blood to enter, said right inlet port having means for attachment to the right atrium, one posterior outlet port for blood to exit said right blood chamber, said posterior outlet port being located above and behind the right inlet port, said posterior outlet port having means for attachment to the main pulmonary artery, said posterior outlet port either including or being adjacent to the valve for the main pulmonary artery, one left blood chamber, said left blood chamber having an elongated shape essentially directed up and to the right, said left blood chamber having one left inlet port for blood to enter, said left inlet port having means for attachment to the left atrium, one anterior outlet port for blood to exit said left blood chamber, said anterior outlet port being located above and to the right of the left inlet port, approximately at the same height as and in front of said posterior outlet port, said anterior outlet port having means for attachment to the aorta artery, said anterior outlet port either including or being adjacent to the valve for the aorta artery, the spatial arrangement between said blood chambers being such that, when they are simultaneously fully expanded, a part of the right blood chamber (i.e., which projects onto the anterior thoracic wall and coincides with the projection onto said anterior thoracic wall of a corresponding part of the left blood chamber) is posterior to said corresponding part of the left blood chamber.

In particular, the artificial heart of the instant invention comprises an assembly of two artificial ventricles or blood chambers, each having an inlet and an outlet. The incoming blood from the right auricle enters the right blood chamber through the right inlet port and exits it through the posterior outlet port. The incoming blood from the left auricle enters the left blood chamber through the left inlet port and exits it through the anterior outlet port.

The unique spatial arrangement of both blood chambers, inlet ports and outlet ports give the instant invention a radically better utilization of the space available inside the mediastinum after having surgically removed both native ventricles and having surgically liberated both great vessels, main pulmonary artery and aorta artery. An important advantage of the instant invention consists on the location of the posterior outlet port, which is placed posterior and above to the right inlet port. This specific placement enables the utilization of the space available above both auricles for blood pumping purposes, which otherwise would be unutilized. This arrangement places the posterior outlet port in the space normally occupied by the initial sector of the aorta artery. From that native posterior position, the aorta artery travels upwards and forward to the right to exit the anterior mediastinum. The anterior outlet port is placed approximately at the same height to and in front of the posterior outlet port. Hence, the lower sectors of the aorta artery and main pulmonary artery are surgically liberated and transposed with respect to their antero-posterior position so as to connect them to their corresponding outlet ports. If additional space is desired, the initial sector of both great vessels will be removed and both outlet ports will be placed at a higher position, close to a plane located at the level of the right pulmonary artery and the mid sector of the ascending aorta artery.

Another important advantage of the instant invention consists on the shape and location of both blood chambers which enables a significantly better utilization of the space available in the mediastinum. In their fully expanded position both blood chambers reach the anterior thoracic wall. The right blood chamber has an elongated shape, essentially directed up and back. The left blood chamber has an elongated shape, essentially directed up and to the right. The aorta artery, in its upward path, occupies an anterior position at its crossing of the right pulmonary artery. Therefore, the space available inside the mediastinum is significantly better utilized in the instant invention by keeping the pathway of the blood coming from the right auricle into the main pulmonary artery into an posterior position with respect to the pathway of the blood coming from the left auricle into the aorta artery. Systemic and pulmonary pathways do not comply with this requirement in the native ventricles and the previous art in the field of Total Artificial Hearts has not changed it either. The instant invention changes this native disposition, placing the right blood chamber always behind the left blood chamber, when their projections onto an anterior thoracic wall coincide. In doing so the instant invention is able to utilize the space available for pumping blood and not merely transporting it through artificial tubes to reach its intended destination.

The volume available for pumping in the instant invention is further increased by placing the outlet ports close to the valves leading to the great vessels. Therefore, because of the described arrangement of the different components comprising the instant invention, the pumping volume provided by the blood chambers actually reach higher in the mediastinum than in the previous art.

The better use of the space available in the mediastinum enables the Total Artificial Heart of the instant invention to have a higher final diastolic volume of the blood chambers, obtaining in this way ejected volumes large enough to achieve an acceptable blood flow rate without a significant increase of the heart frequency, and thereby reducing both hemolysis and mechanical wear of movable parts.

Furthermore, in the preferred embodiment of the instant invention and in some variant, this Orthotopic Total Artificial Heart can be completely placed inside the mediastinum, i.e. the blood chambers, the driving mechanism, for example the compressing mechanism, and power source. In this manner, the instant invention can be an integrated, "one-piece" system.

The significantly better space utilization of the instant invention is used for at least one of two purposes: a) To place the driving mechanism for the Total Artificial Heart inside the mediastinum; b) To increase the diastolic volume of each blood chamber. This new design realizes a fundamental need expressed by the medical community for the necessary anatomical fit of the Total Artificial Heart with the available and restricted space of the mediastinum.

Due to the different structural layout of the Total Artificial Heart of the instant invention, the following important improvements are made:

1—Keeping the pathway of the blood coming from the right auricle into the main pulmonary artery in a posterior position with respect to the pathway of the blood coming from the left auricle into the aorta artery 2—Outflow tract paths of the artificial ventricles are placed closer to the circulatory system that is going to be irrigated, therefore not needing prosthetic tubes to reach the corresponding arteries.

3—The artificial ventricles are placed in a higher position inside the mediastinum.

4—In the preferred embodiment and other variants of the instant invention, both the outer compressing chamber and the power source are also placed inside the mediastinum.

Furthermore, if necessary, additional space can be conveniently created by resecting the initial sector of the large arterial trunks.

An important hemodynamic and hematological advantage of the instant invention is that, by placing the blood chambers' outflow near the systemic and pulmonary vascular regions, it no longer requires the use of prosthetic tubes at the outflow of these blood chambers. This characteristic provides the instant invention with the great advantage of being directly connected with the vascular systems through native vessels which respond to increased blood flow with the vasodilatation autonomous reflex response. Hence, no increased pressures are needed to get a higher blood flow, thereby reducing the pressure on the walls of the blood chambers and the turbulence and associated liquid shear stress, all of which greatly reduces the subsequent damage that this causes to blood cells and to the life of the Total Artificial Heart itself.

The artificial ventricles of the instant invention are one-piece blood chambers that have two non-thrombogenetic characteristics, their morphology and their surfaces in contact with the blood. The blood chambers are elongated with an upward shape, having neither stasis areas nor corners or boundaries between dissimilar materials; neither they have stitches among them.

Another advantage of the instant invention is the non-trombogenic walls of the blood chambers. These inner walls are made with biological surfaces, soft and flexible, which protect blood cells and red corpuscles against cellular traumatism, therefore avoiding hemolysis. In addition, the cellular damage is reduced in the instant invention because blood is pumped by the action of forces homogeneously distributed and approximately concentric and also because the blood chambers are elongated and made of a single material without corners, borders or stitches, and without prosthetic materials or tubes of a more or less fixed diameter at the outflow of the blood chambers.

Yet another advantage of the instant invention also provides for the independent variation of the discharging volumes of each blood chamber. Such independent handling of the volumetric flow rates for each blood chamber enables the compensation of the imbalance in the blood flow circulating through the pulmonary circuit and the systemic circuit. Physiological differences and shunts between these circulatory circuits shall be compensated in such a way that there shall be no need for creating surgical shunts.

Additional objects and attendant advantages of the present invention will be set forth, in part, in the description that follows, or may be learned from practicing or using the present invention. The objects and advantages may be realized and attained by means of the instrumentalities, features and/or combinations particularly pointed out in the appended claims. It is to be understood that the foregoing general description and the following detailed description are exemplary and explanatory only and are not to be viewed as being restrictive of the invention, as claimed.

BRIEF DESCRIPTION OF THE DRAWINGS

The accompanying drawings, which are incorporated in, and constitute a part of the specification, illustrate embodiments of the present invention and, together with the description, serve to explain the principles of the present invention.

FIG. 3.A Clarification of FIG. 3, showing an anterior view of the preferred embodiment of the instant invention, in a diastolic or filling position of the blood chambers, with the driving mechanism implanted in the systemic-pulmonary circulatory system of a human being, in which the initial sector of the large vessels is removed.

FIG. 3.B Clarification of FIG. 3, an anterior view of the preferred embodiment of the instant invention, in which an ejection or emptying position of the blood chamber, is shown.

FIG. 3.C Representation of an electro-hydraulic variant of the instant invention, in which the compressing effect is produced by two lateral moving surfaces, implanted in the systemic-pulmonary circulatory system of a human being, where the initial sector of the large vessels is removed.

FIG. 3.D Representation of a pneumatic variant of the instant invention, where the compressing effect is produced by the introduction of a compressing fluid inside the outer compressing chamber, which has semi-rigid walls.

FIG. 5.A Inner and right side view of the two blood chambers of the instant invention shown in a diastolic or filling position.

FIG. 6.A Clarification of FIG. 6, showing an upper, rear and left side view of the outer compressing chamber.

FIG. 6.B Upper, rear and left side view of the outer compressing chamber of the electro-hydraulic variant of the instant invention, showing displacement of a moving surface.

FIG. 7.A Clarification of FIG. 7 showing the right side view of the outer compressing chamber of the electro-hydraulic variant of the instant invention.

FIG. 7.B Right side view of the outer compressing chamber of the electro-hydraulic variant of the instant invention, showing displacement of a moving surface.

FIG. 8.A Schematic comparison of the spaces created after having surgically removed both ventricles, before and after the surgical removal of the initial sectors of the aorta artery and the main pulmonary artery.

FIG. 8.B View of the free spaces created by removal of the initial sector of the large vessels.

DETAILED DESCRIPTION OF THE INVENTION

This invention is herein described in detail, as a non-limiting model and as the preferred way to develop it at present. It is also illustrated in the pictures attached hereto.

At present, the specific and preferred way to build the Orthotopic Total Artificial Heart, according to this invention, is the one illustrated as a model in the pictures attached hereto. Notwithstanding, the present invention may be subject to different shape and size modifications and the present specifications are not intended to limit the invention to the particular shapes and/or sizes herein described. On the contrary, the intention is to cover all modifications and alternative executions that are within the spirit and the purpose of the invention in accordance with the claims attached hereto.

Moreover, as there shall be several modifications and changes that shall be analyzed by the technicians in this field, we do not wish to limit the invention to the exact construction or operation described herein. Therefore, any and all equivalent modifications shall be considered as included within the scope of the instant invention.

Figure 1:
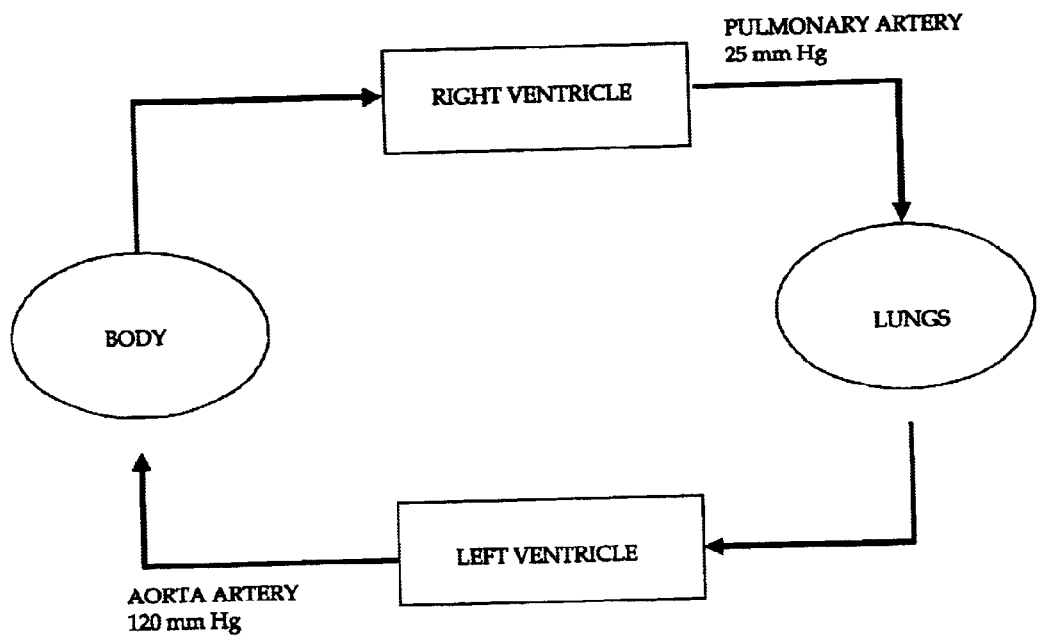
FIG. 1 Schematic representation of the systemic-pulmonary circulatory system of a human being.
Figure 2:
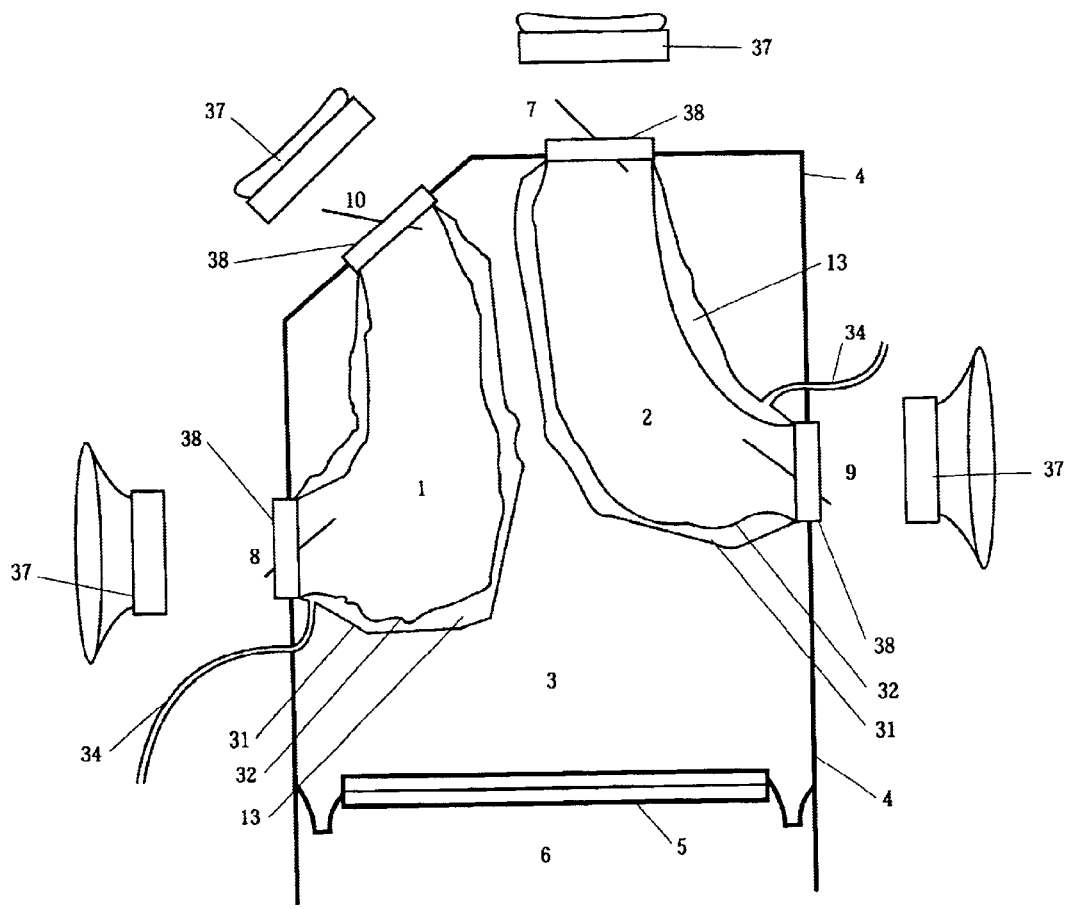
FIG. 2 General schematic representation of the preferred embodiment of the electro-hydraulic variant of the instant invention.

The electro-hydraulic preferred embodiment of the Orthotopic Total Artificial Heart, as shown in the schematic representation of FIG. 2, comprises, an outer compressing chamber 4, a compressing fluid 3, two blood chambers, right 1 and left 2, and a mechanism for independently varying their discharging volumes.

Figure 3:
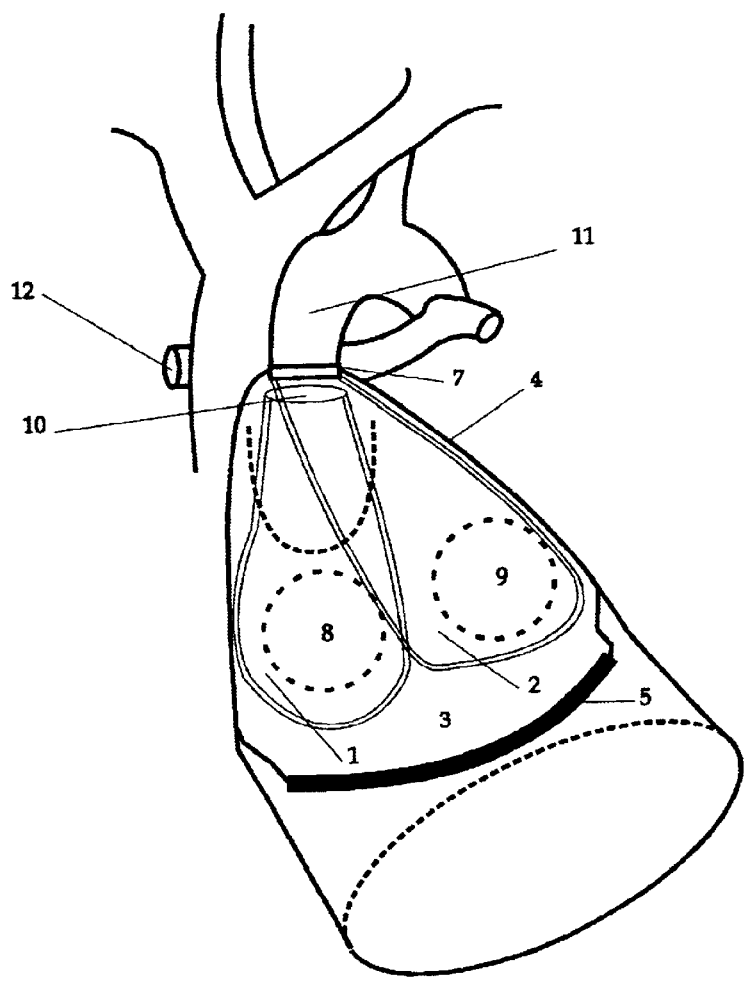
FIG. 3 Anterior view of the preferred embodiment of the electro-hydraulic variant of the instant invention, implanted in the systemic-pulmonary circulatory system of a human being, in which the initial sector of the large vessels is removed.
Figure 3:
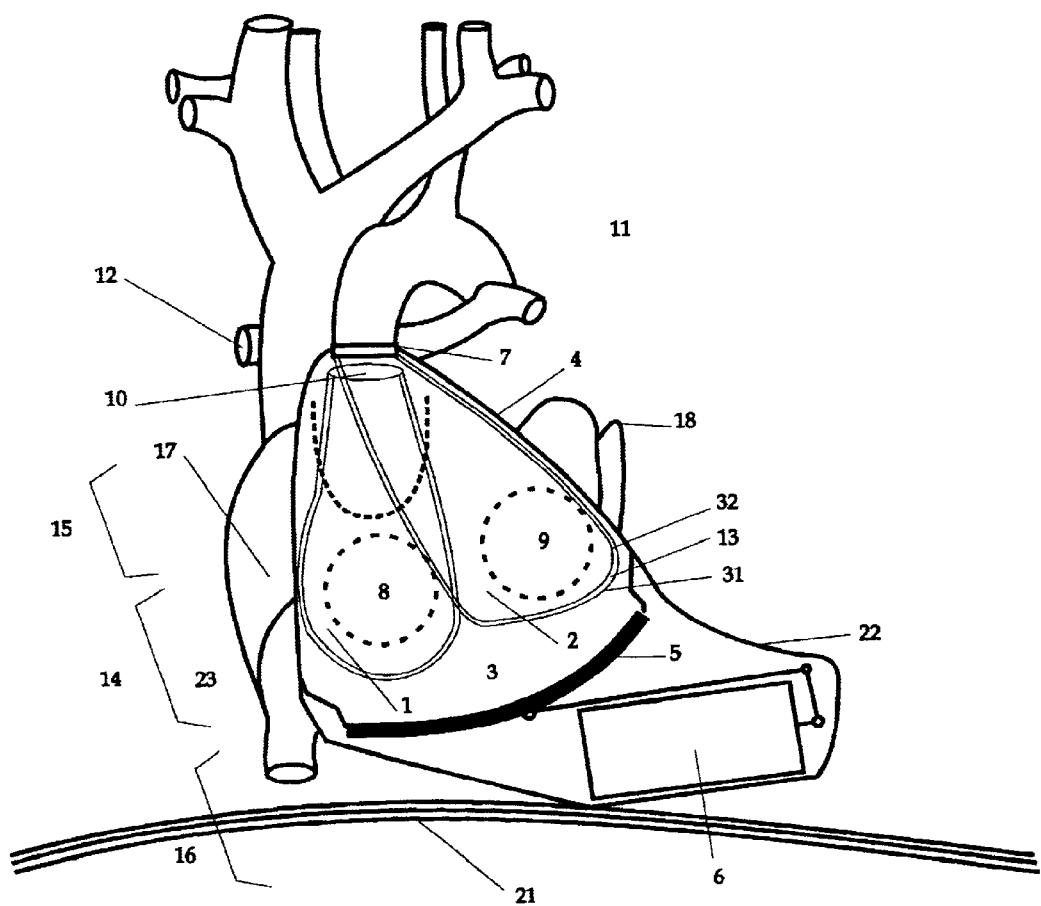
Figure 3:
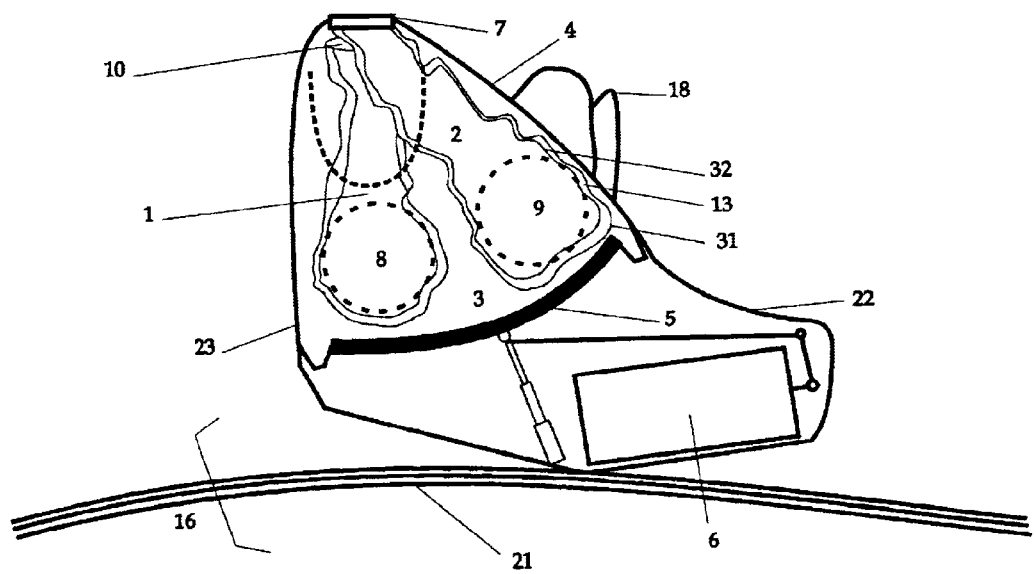
Figure 3:
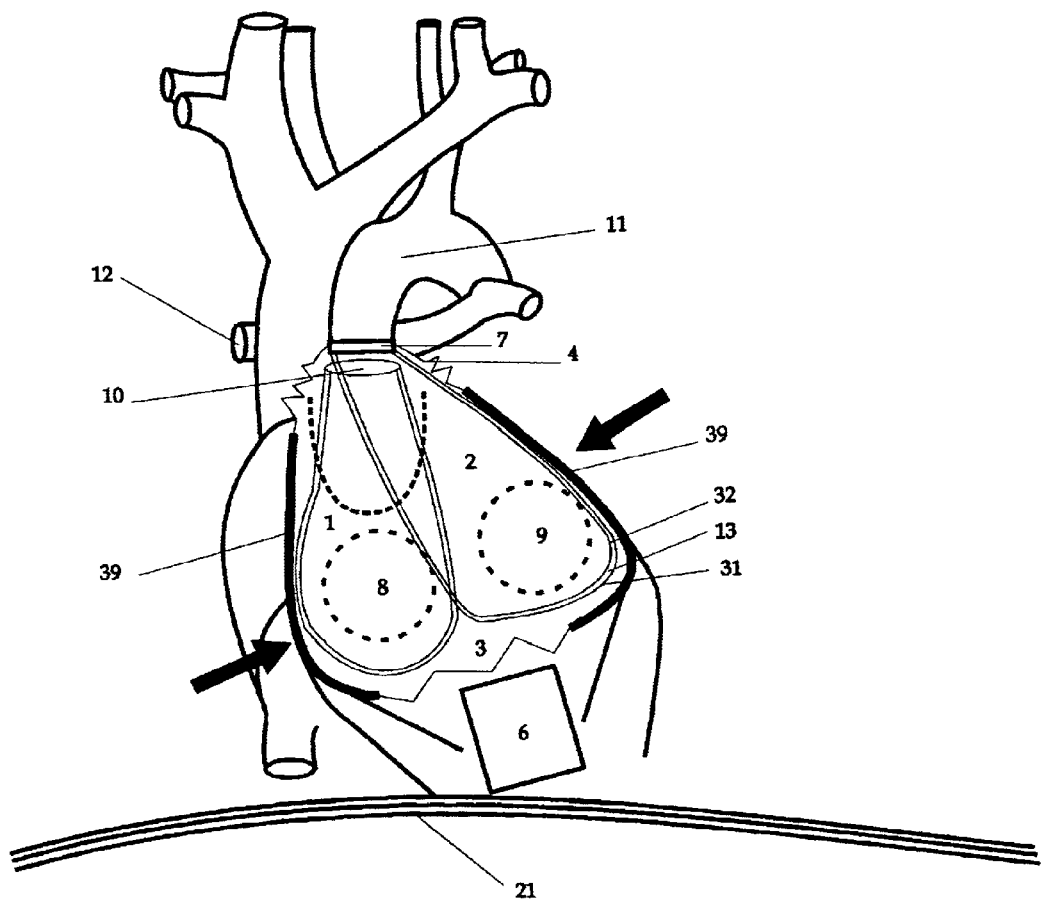
Figure 3:
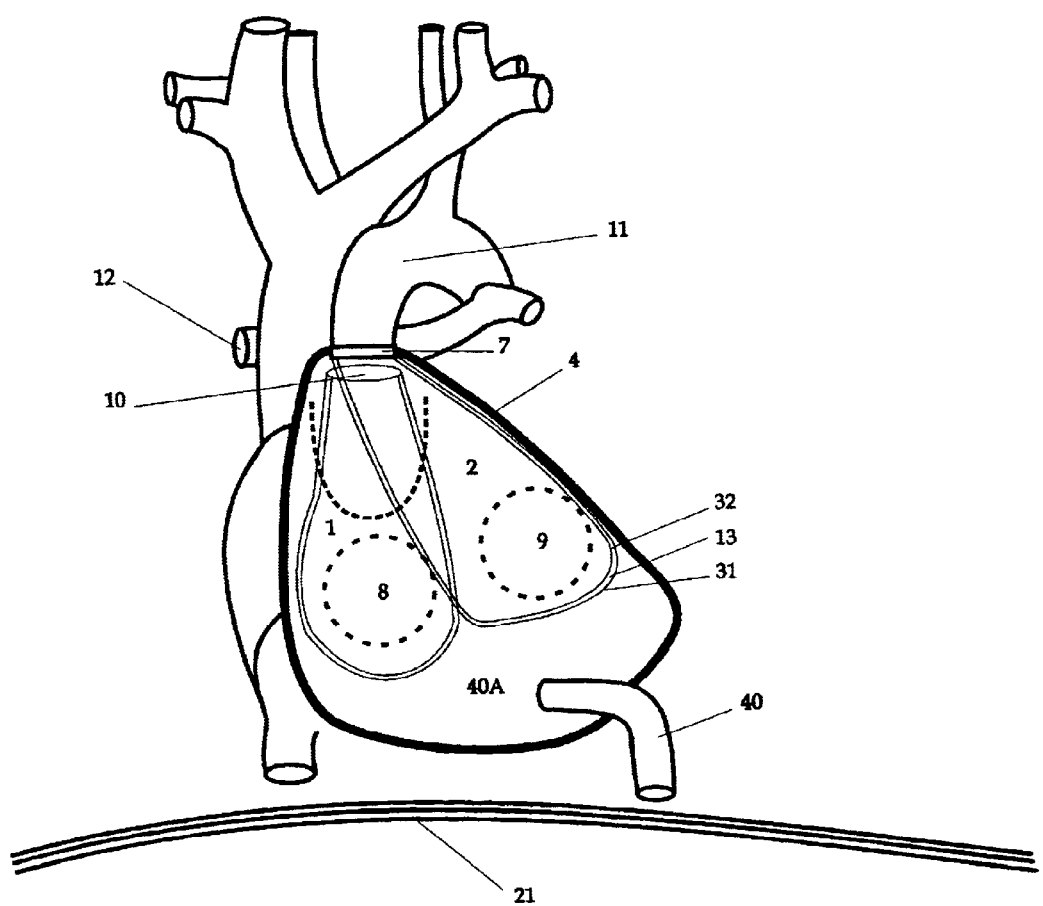
Figure 4:
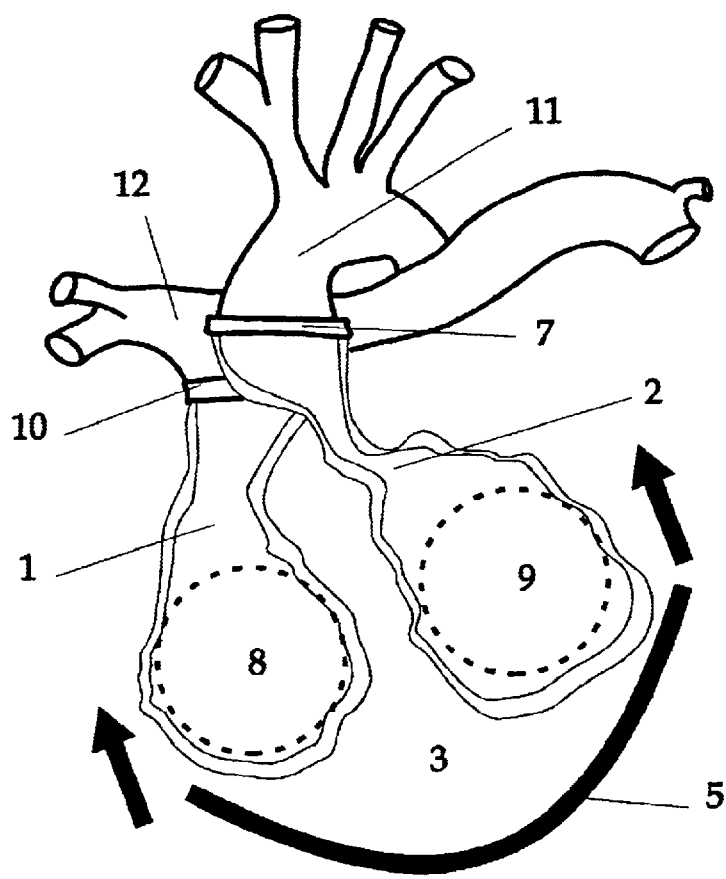
FIG. 4. Inner and anterior view of the two blood chambers of the instant invention seen in an ejection or emptying position.

The outside wall of the instant invention is an outer compressing chamber 4, the external shape of which has an anatomy which agrees with the mediastinal space that it shall occupy, as shown in FIGS. 3, 3.A, 3.B, 6, 6.A, 6.B, 7, 7.A and 7.B, with an oval or kidney or pyramidal shape, with a upper vertex and a lower and left base. It will occupy the space called anterior mediastinum.

The outer compressing chamber 4 of the preferred embodiment of instant invention is constituted by different sectors, as observed in FIG. 3 and 3.A: a mid sector 14, which is placed in front of the right auricle 17 and left auricle 18; an upper sector or vertex 15, which is raised up to a horizontal plane crossing at the right pulmonary artery's lower border level 12, and is extended in the front up to the breastbone 24 (see FIGS. 7.A and 7.B); a lower sector or base 16 which is extended up to the diaphragm 21 and the area of the native heart end, occupying the supradiaphragmatic free space 33 (see FIG. 8.B) created by removing the 2 native ventricles. In all these figures of the preferred embodiment, FIGS. 3, 3A, 3B, 4, 5, 5A, the initial sector of both great vessels has been surgically removed, as seen in FIG. 8B.

The outer compressing chamber 4, as shown in a frontal view in FIGS. 3, 3.A and 3.B, has its left edge 22 moving from left to right as it ascends distancing itself from the diaphragm 21 and reaches close to the left edge of the aorta artery at its upper part. The right edge 23 of said outer compressing chamber 4 travels up more or less vertically from the diaphragm level 21.

Figure 7:
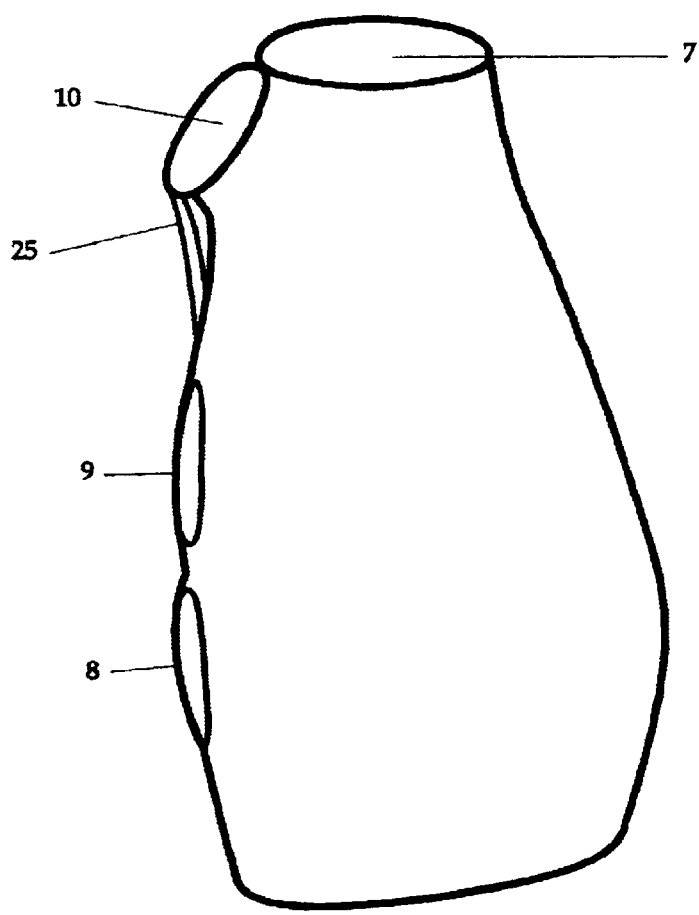
FIG. 7 Right side view of the outer compressing chamber of the electro-hydraulic variant of instant invention.
Figure 7:
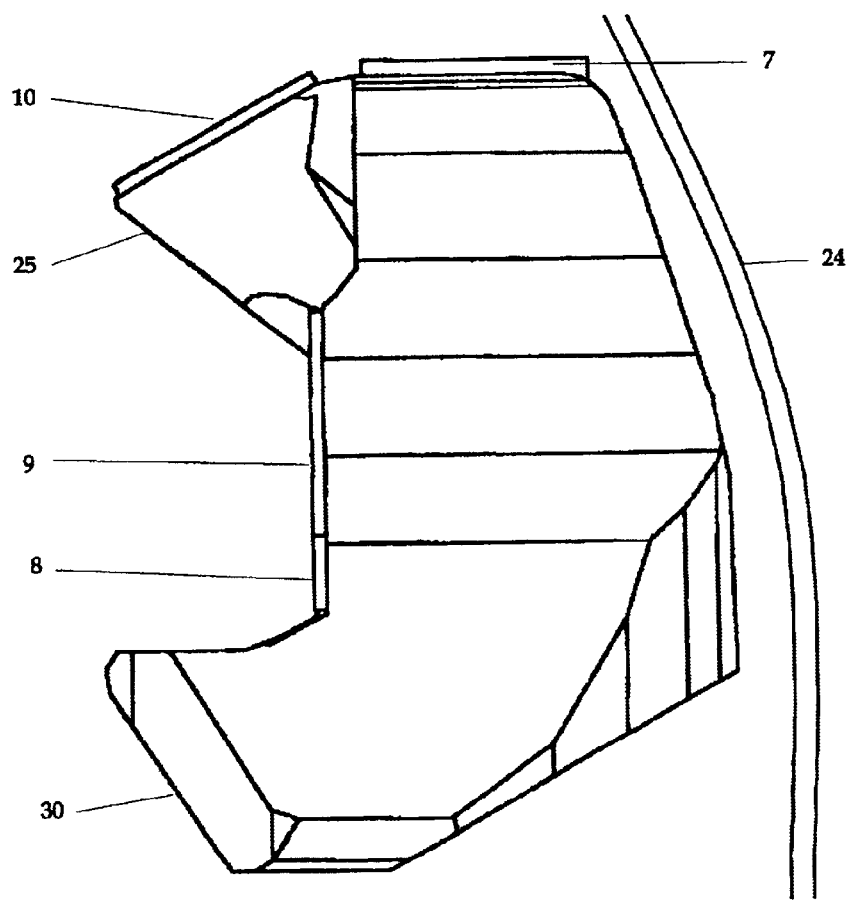
Figure 7:
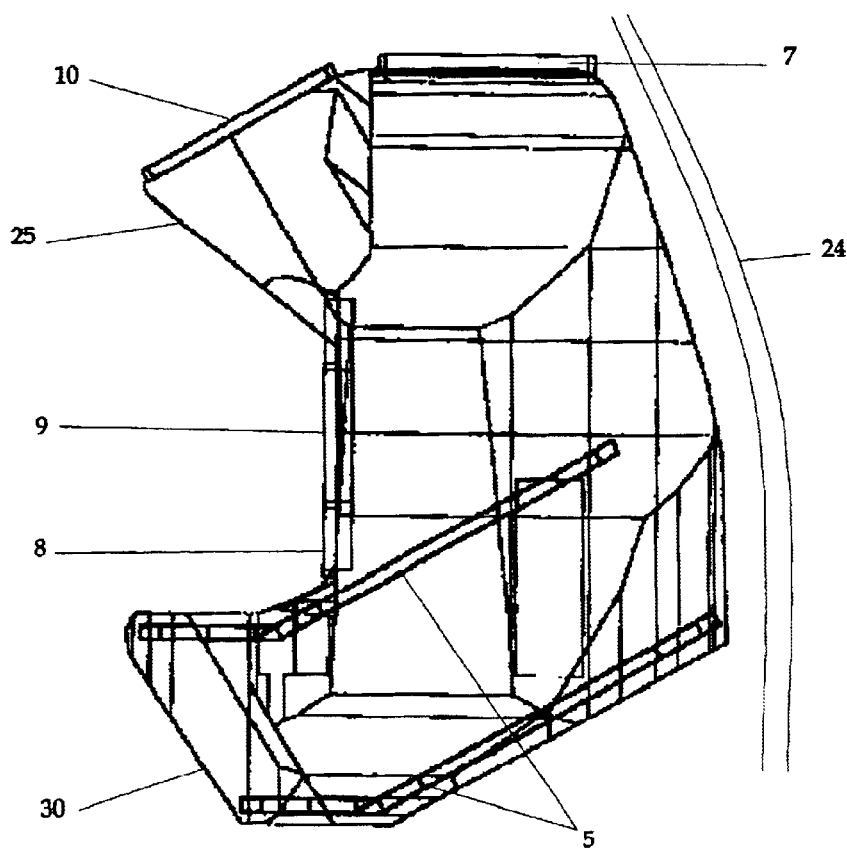
Figure 8:
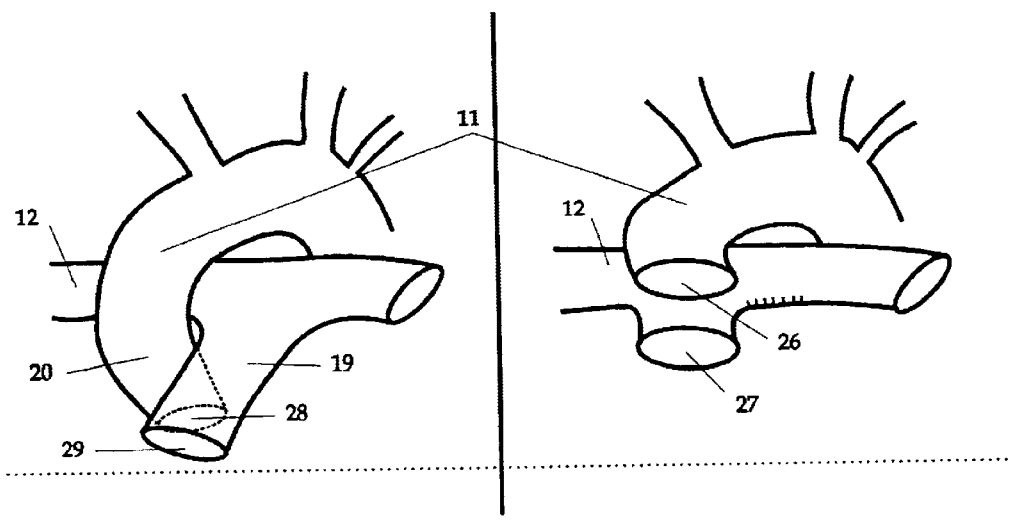
FIG. 8 Schematic comparison between the aorta artery and the main pulmonary artery before and after the surgical removal of their initial sectors.
Figure 8:
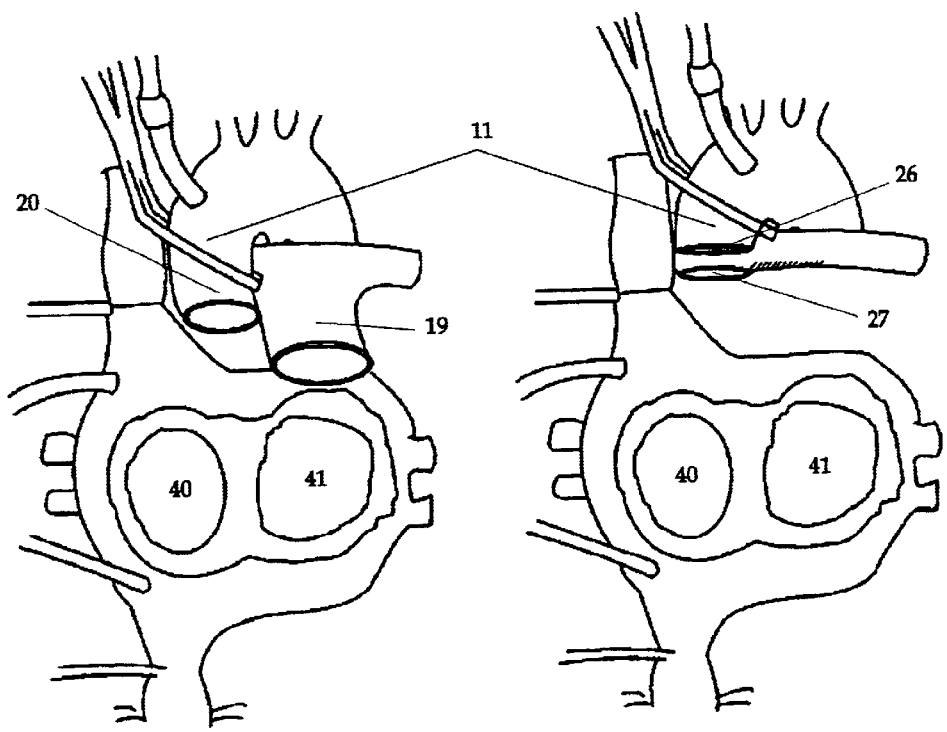
Figure 8:
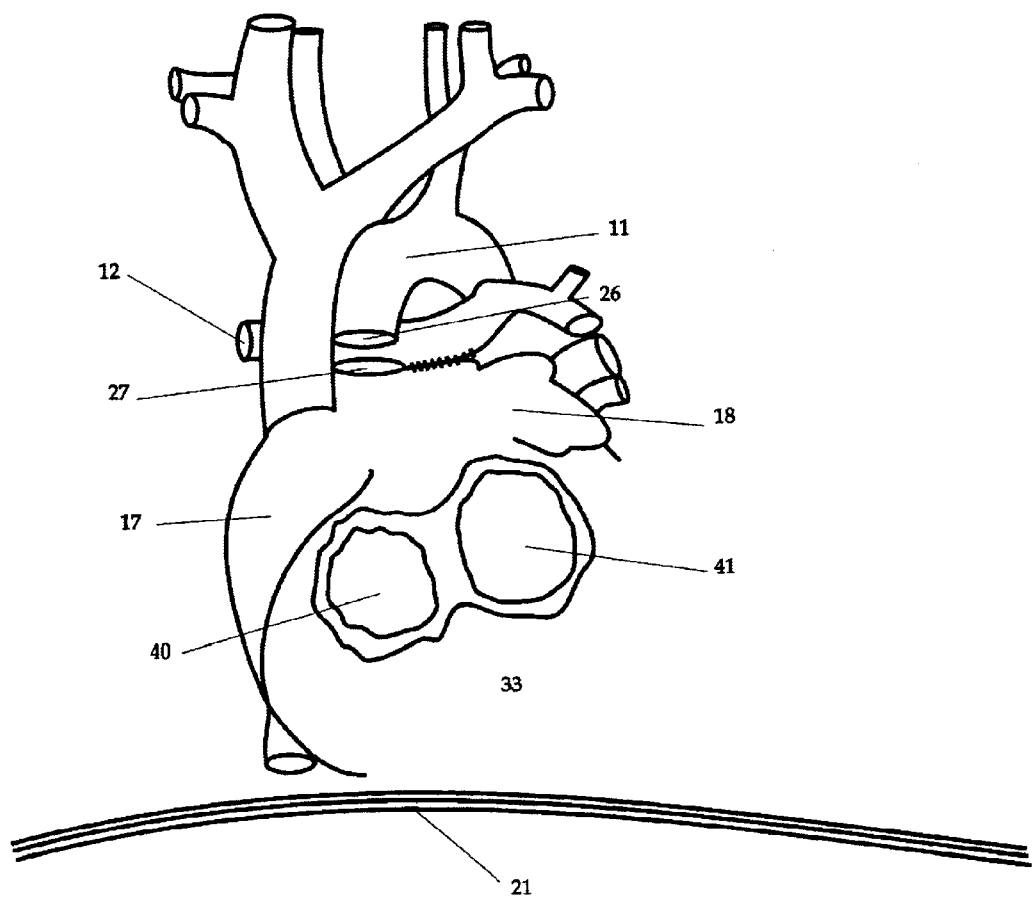
Figure 9:
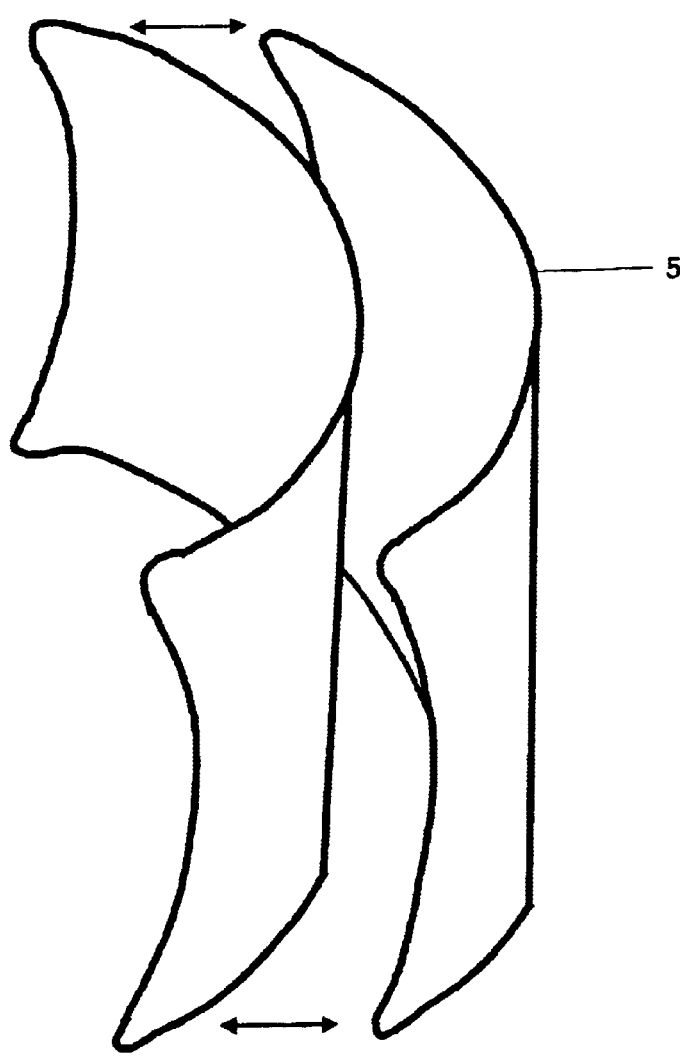
FIG. 9. View of the moving surface of the compressing mechanism of the preferred embodiment of the instant invention.

The outer compressing chamber 4's depth is extended from the right 8 and left 9 auricular-ventricular inlet ports to the breastbone 24, as shown in FIGS. 7, 7.A and 7.B.

Figure 6:
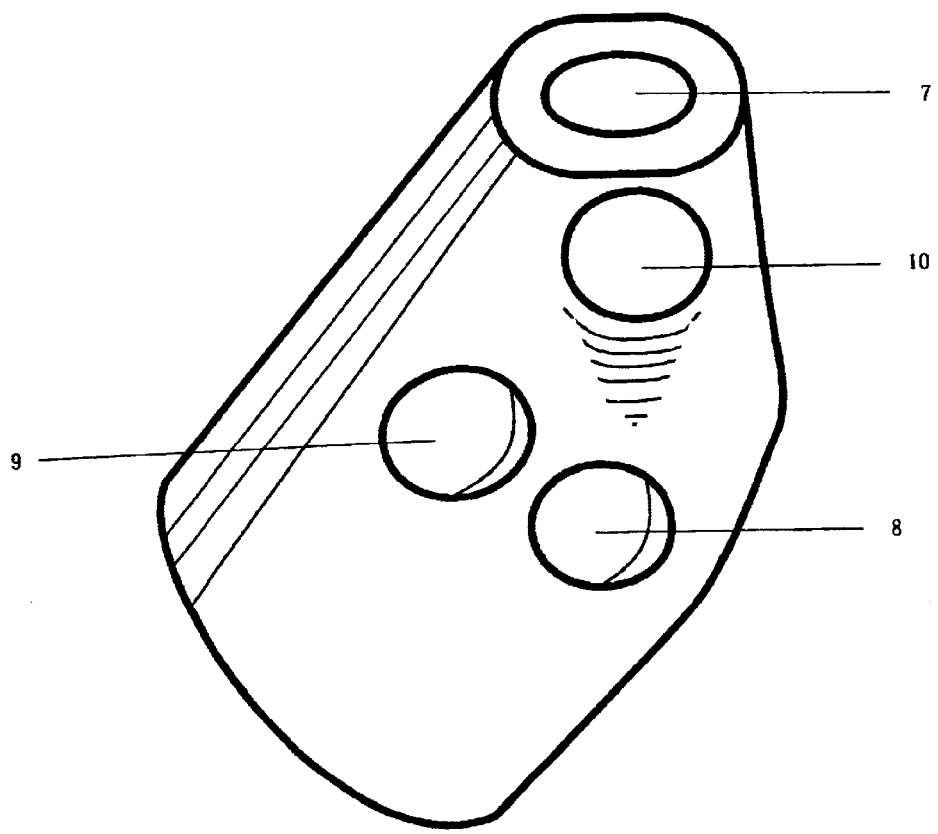
FIG. 6 Upper, rear and left side view of the outer compressing chamber of the electro-hydraulic variant of the instant invention.
Figure 6:
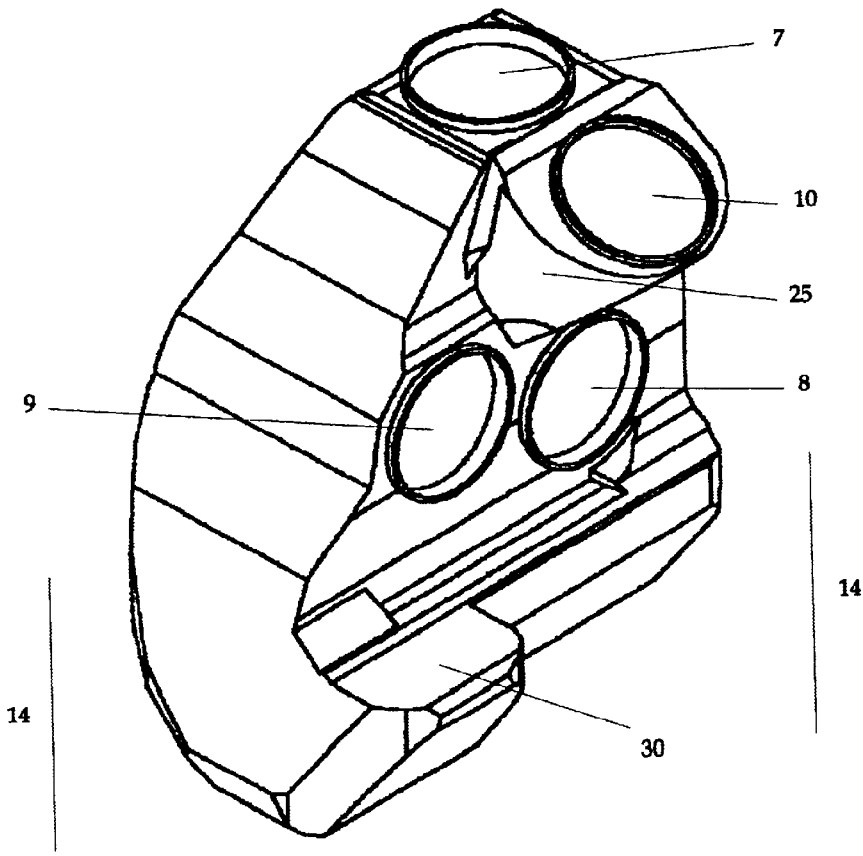
Figure 6:
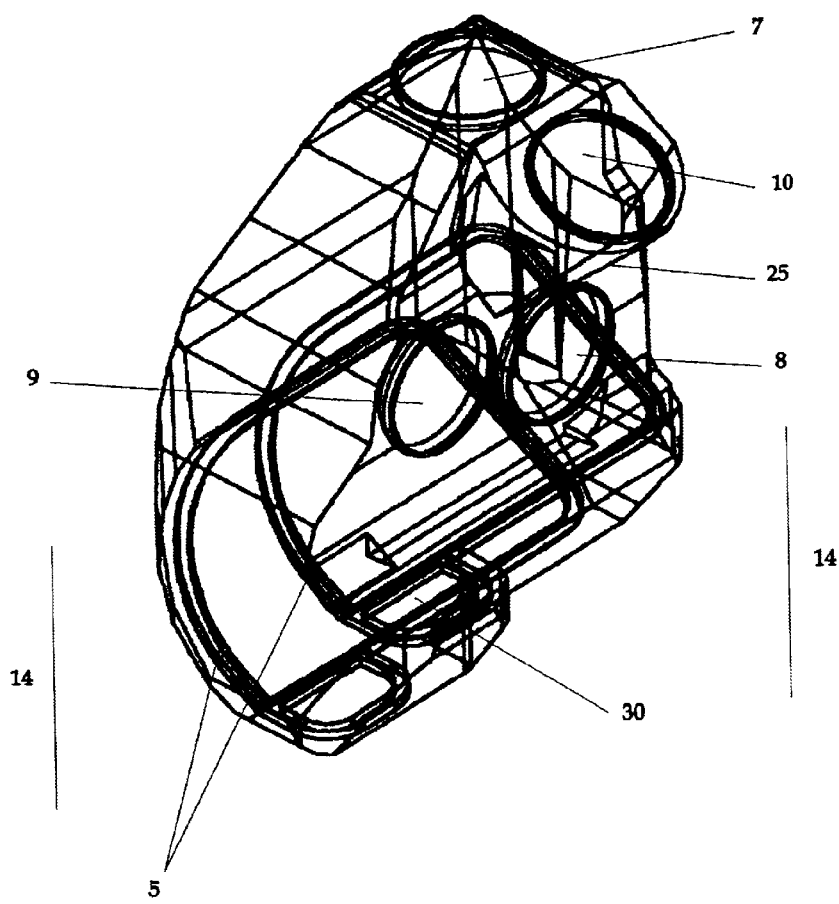

The rear side, in its upper and right sector, above the right inlet port 8 of the right blood chamber 1, as shown in FIGS. 6, 6.A, 6.B, 7, 7.A and 7.B, presents a geometric structure, a cone trunk 25, which creates a growing and oblique protuberance, to the upper and to the rear parts. In the upper edge of this cone trunk 25, the posterior outlet port 10 of the right blood chamber 1 is located and connected directly to the pulmonary circulatory circuit.

Figure 5:
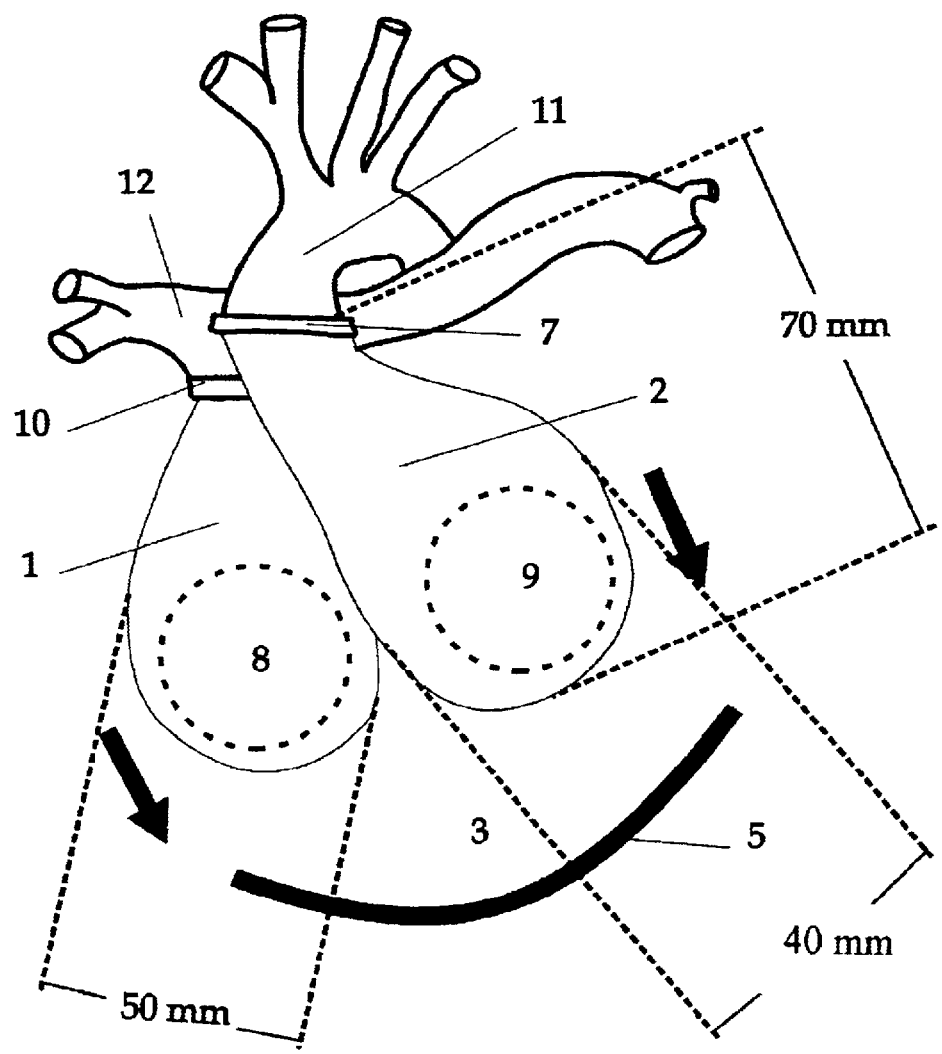
FIG. 5. Inner and anterior view of the two blood chambers of the instant invention seen in a diastolic or filling position.
Figure 5:
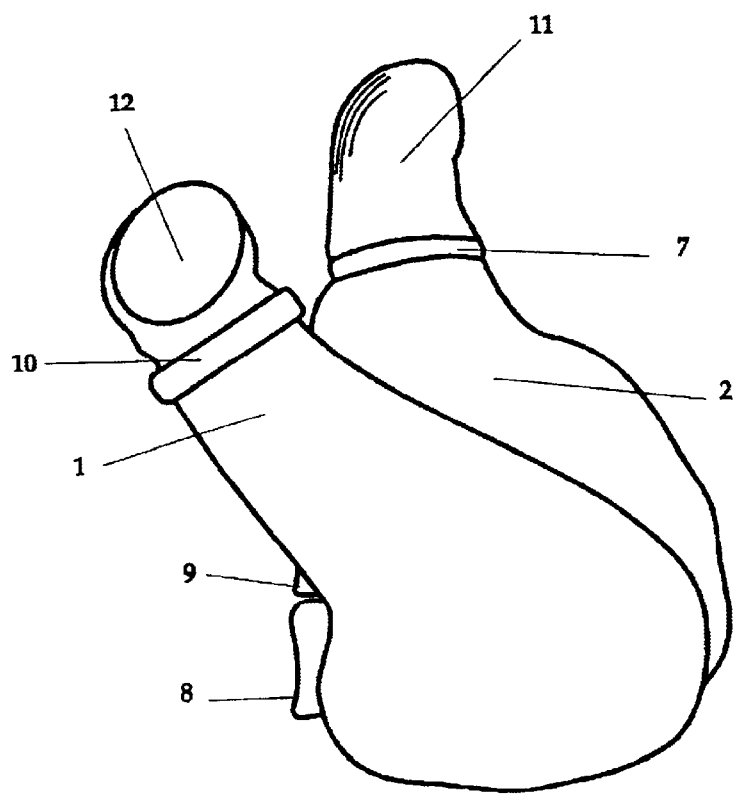

The outer compressing chamber 4, as shown in the FIG. 2 outline, has four holes, two inlets and two outlets, for the connection of blood chambers to the patient's circulatory systems,. The inlet ports 8 and 9 are placed on the rear side of the present invention, as shown in FIGS. 5.A, 6, 6.A, 6.B, 7, 7.A and 7.B. The right inlet port 8 of the right blood chamber 1 receives blood from the right auricle 17. The left inlet port 9 of the left blood chamber 2, receives blood from the left auricle 18, as shown in FIGS. 3.A and 8B.

The outlet ports 7 and 10 are located in the upper side of outer compressing chamber 4, as shown in FIGS. 3, 3.A, 3.B, 6, 6.A, 6.B, 7, 7.A and 7.B. The anterior outlet port 7 of the left blood chamber 2, connects through the neoentrance 26 (see FIGS. 8, 8.A and 8.b) to the systemic circulatory circuit. The posterior outlet port 10 of the blood chamber 1, is located in the upper part vertex of the cone trunk structure 25, which creates a protuberance in the rear side of the outer compressing chamber 4, and is connected through the neoentrance 27 with the pulmonary circulatory circuit, as shown in FIGS. 8, 8.A and 8.B.

After removing the initial sector of the great vessels, neoentrance 26 and neoentrance 27 are in a higher position than that of the aortic valve 28 and the pulmonary valve 29, as shown in FIGS. 8 and 8.A.

As shown in FIGS. 3, 3.A, 3.B, 4, 5 and 5.A, posterior outlet port 10 of the instant invention is behind the anterior outlet port 7, that is they are in an inverted position compared to the outlet valves of the native ventricles.

Inside the outer compressing chamber 4 of the preferred embodiment of the instant invention, as shown in the outline represented in FIG. 2, there are the compressing fluid 3, and two structures with the shape, size, walls and connections of the instant invention, the right blood chamber 1 and the left blood chamber 2. They occupy the whole inner volume of this outer compressing chamber 4, which is sealed.

The compressing fluid 3 (for example glycerin), as shown in the schematic representation of FIG. 2, occupies the volume defined by the inner side of outer compressing chamber 4, the moving surface 5, and the external walls 31 of both blood chambers. This compressing fluid 3 is used to transfer the driving force of the moving surface 5 to the external walls 31 of both blood chambers. The compressing fluid contained inside the outer compressing chamber 4, acts in such a way that when the moving surface 5 is in a filling or diastolic position, as shown in FIGS. 3, 3.A, 5 and 5.A, it allows the right 1 and the left 2 blood chambers to reach each of them a volume of 90 cc, when the blood enters through the right inlet port 8 of the right blood chamber 1 and through the left inlet port 9 of the left blood chamber 2. Both blood chambers shall have their respective outlet ports 10 and 7 closed.

While the moving surface 5 moves 3 centimeters forward inside the outer compressing chamber 4, reaching its maximum blood ejection or systolic position, as shown in FIGS. 3.B and 4, it transfers the forces received from the driving mechanism to the compressing fluid 3, which shall compress the external wall 31 of the right 1 and left 2 blood chambers producing the emptying effect of their inner volume, obtaining in such a way the expulsion or ejection of the blood contained inside them, through the posterior outlet port 10 of the right blood chamber 1, and the anterior outlet port 7 of the left blood chamber 2. Both blood chambers shall have their respective inlet ports closed.

The right blood chamber 1 is a soft and flexible sac created to pump the blood, and is placed in front and above the position of the right auricle, to the right in the outer compressing chamber 4, as shown in FIGS. 3, 3A, 3B, 4, 5 and 5A. It is composed of two soft and flexible walls, its inner cavity has no corners, stitches or boundaries between the different materials, as its inner biological membrane 32 shall be totally constituted by a single-piece pig pericardium. Its external wall 31 is a synthetic one, made of Pebax 3533, for example. This right blood chamber 1 is connected through its right inlet port 8 to the right auricle 17 and through its posterior outlet port 10 to the pulmonary circulatory. Said right blood chamber 1, when fully expanded, reaches the anterior thoracic wall and has an elongated shape essentially directed up and back. As shown in FIGS. 3, 3A, 3B, 4, 5 and 5A, this right blood chamber 1 shall have a significant difference with the anatomic structure of the native right ventricle. Its blood flow pathway goes up and back from the right inlet port 8, almost in a straight line as shown in FIGS. 3, 3.A, 3.B, 4, 5 and 5 A, until reaching and connecting directly to the neoentrance 27 of the pulmonary circulatory system, which occupies a posterior position inside the mediastinum, as shown in the schematic comparison of FIGS. 8 and 8.A. Therefore, we avoid the loop originated in the embryonic circulatory tube, or downward path that the blood makes inside the native right ventricle, by entering through the tricuspid valve and descending to the diaphragm 21. The supradiaphragmatic space 33 of the anterior mediastinum shown in FIG. 8.B, is reserved to place the driving mechanism 6 located in the base sector 16 of the preferred embodiment of the instant invention, as shown in FIGS. 3, 3.A and 3.B.

The left blood chamber 2 is also a soft and flexible sac created to pump blood, and is placed in front and above the position of the left auricle located to the left in the outer compressing chamber 4. As shown in FIGS. 3, 3A, 3B, 4, 5 and 5A, it is composed by two soft and flexible walls, its inner cavity has no corners, stitches or boundaries between different materials since the inner biological membrane 32 is totally composed by a single-piece pig pericardium. Its external wall 31 is a synthetic one, made of Pebax 3533, for example. From its left inlet port 9 or mitral valve, which connects it to the left auricle 18 as shown in FIGS. 3, 3.A, 3.B, 4, 5 and 5.A. Said left blood chamber 2, when fully expanded reaches the anterior thoracic wall and has an elongated shape essentially directed up and to the right in the anterior mediastinum, having its outflow pathway in front of the right outflow pathway. The position of the anterior outlet port 7 is shown in FIGS. 3, 3.A, 4, 5 and 5.A and is placed in front of the posterior outlet port 10. In this way, the left blood chamber 2 also allows the blood flow to be almost straight and in an anterior, upward and right direction, to the systemic circulatory system.

These two blood chambers of the instant invention, right 1 and left 2, soft and flexible, have a double membrane wall, as shown in the schematic representation of FIG. 2, and have an inner cavity the volume of 90 cc each. However, the discharging volume of each blood chamber can be independently varied. To decrease or increase the final diastolic volume of each blood chamber independently, the preferred embodiment of the instant invention has a mechanism for independently varying discharging volumes. In the interstitial space between the inner walls 32 and the external ones 31 of each blood chamber a fluid, called interstitial fluid 13, is introduced through a catheter 34 of the mechanism for independently varying discharging volumes, as shown in the outline of FIG. 2. When the space between the inner wall 32 and the external wall 31 is filled with the interstitial fluid 13, the inner volume of each blood chamber is reduced. When the intersticial liquid 13 is removed by means of the catheter 34 of the mechanism for independently varying discharging volumes, the final diastolic volume of each blood chamber is increased independently. The interstitial fluid 13 may be, for example, glycerin. This mechanism for independently varying discharging volumes is handled through the catheter 34 as shown in the schematic representation of FIG. 2, and inserted, for example, via a central vein. This catheter 34 is introduced into the outer compressing chamber 4, next to the inlets 8 and 9 of the blood chamber, from the neck veins and it is connected to the external wall 31. In this way, during the implantation period and the postoperative period, the physician can vary the interstitial volume of each blood chamber, being able to independently vary their final diastolic volume, to achieve a blood flow in the systemic circuit and in the pulmonary circuit, according to the physiological needs of each patient and the specific operation of each device.

An electro-hydraulic variant in the design of the outer compressing chamber 4 of the instant invention, having two lateral moving surfaces 39 to produce the compressing effect on the two blood chambers, is shown in FIG. 3C. In this outer compressing chamber 4, the lateral moving surfaces 39 are shown in a diastolic position. These two lateral moving surfaces 39 when displaced to the center of the outer compressing chamber 4 increase the pressure of compressing fluid 3, which effects the compressing action of the blood chambers, right 1 and left 2.

Another variation in the design of the outer compressing chamber 4 of the instant invention is shown in FIG. 3D. To produce the compressing effect on both blood chambers, a variation of the volume of the compressing fluid 40A inside the outer compressing chamber 4 is produced. A variation on the volume of the compressing fluid 40A is produced, for example, by gas injection and extraction within the outer compressing chamber 4; this outer compressing chamber 4 is characterized by its ,low volume change upon changes in the internal pressure upon gas injection and extraction. FIG. 3D shows a schematic representation of the outer compressing chamber 4 with the same layout for the right, 1 and the left 2 blood chambers and with one connection for a tube 40 which connects to a source that introduces and extracts gas. FIG. 3D shows the compressing fluid 40 A in the outer compressing chamber 4 which, in this case, is a gas.

Figure 10:
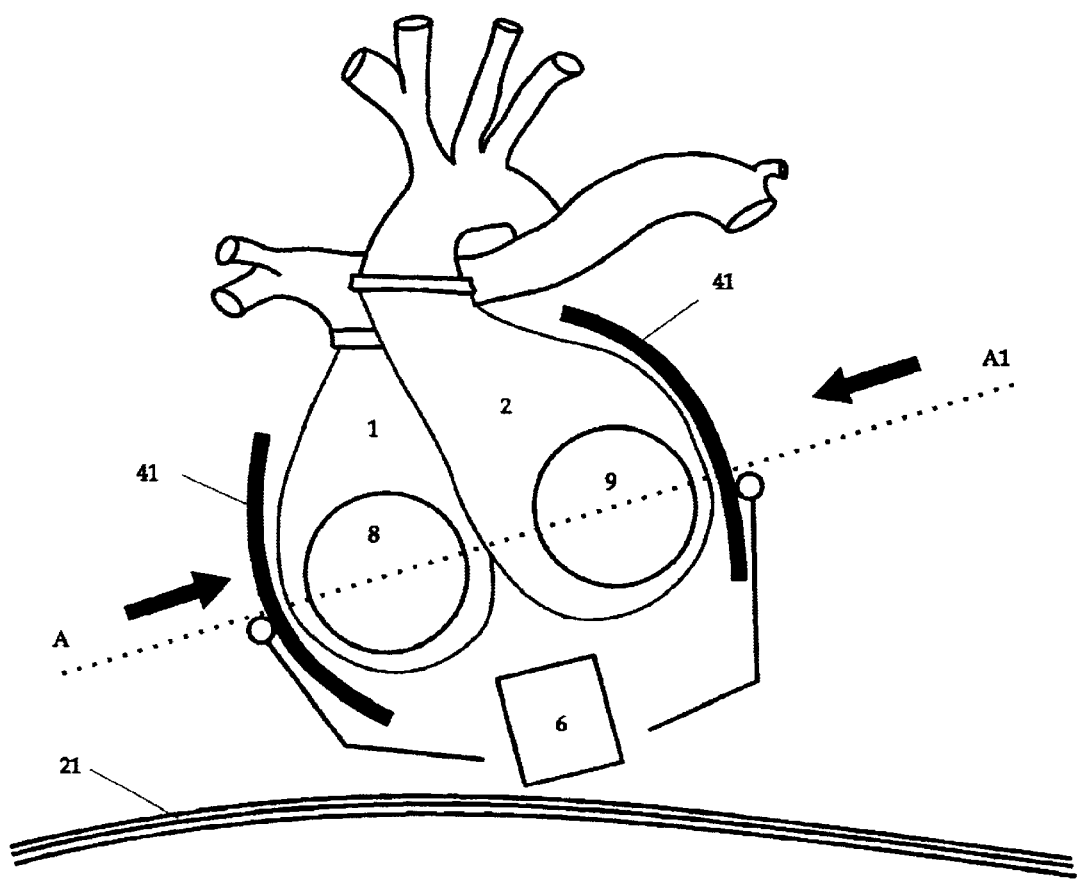
FIG. 10. Anterior view of an electro-mechanic variant of the instant invention, showing the compressing mechanism directly acting on the blood chambers.
Figure 11:
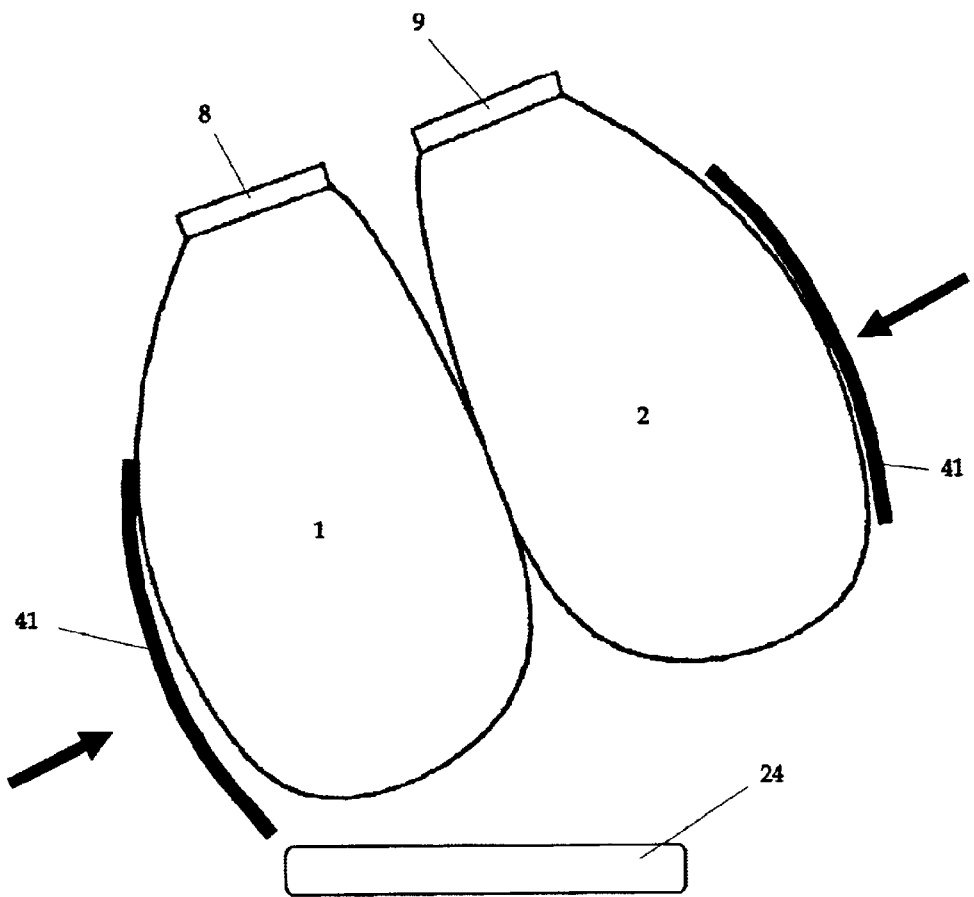
FIG. 11. View of the upper part of the cross section A–A1 in FIG. 10, where a set of two lateral moving surfaces is outlined.
Figure 12:
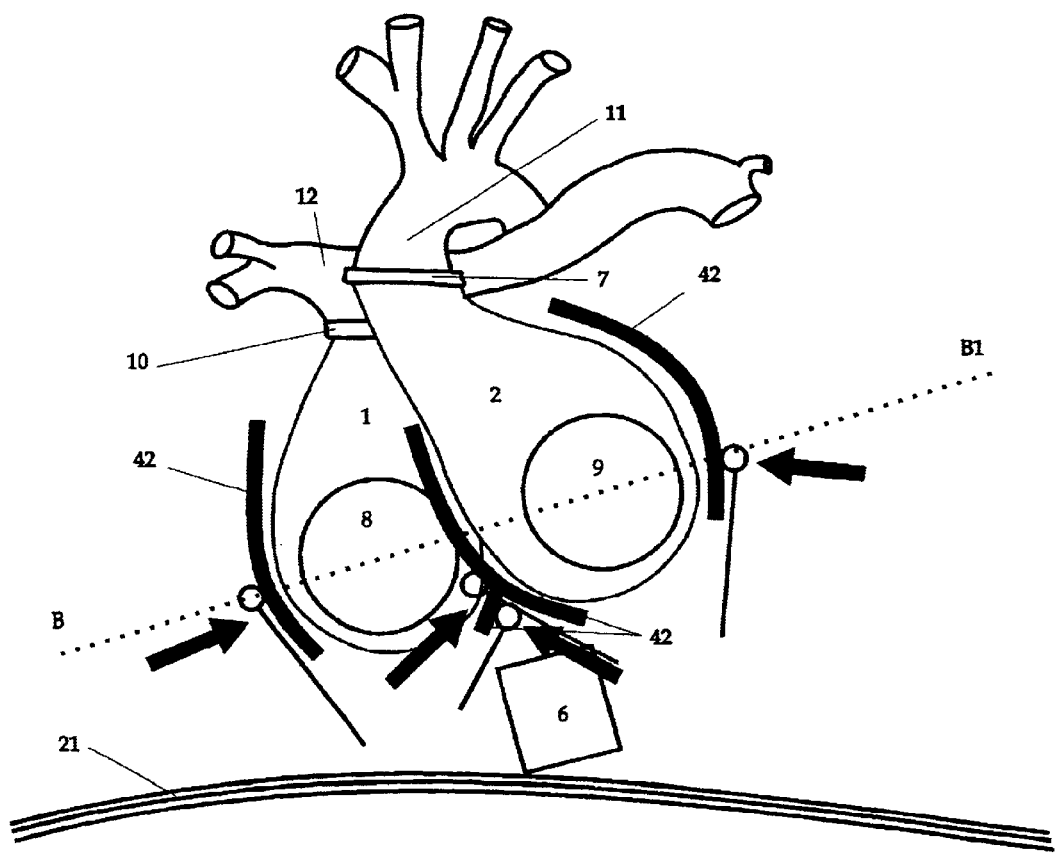
FIG. 12. Anterior view of another electro-mechanic variant of the instant invention, showing an independent double-compressing mechanism directly acting on each blood chamber.
Figure 13:
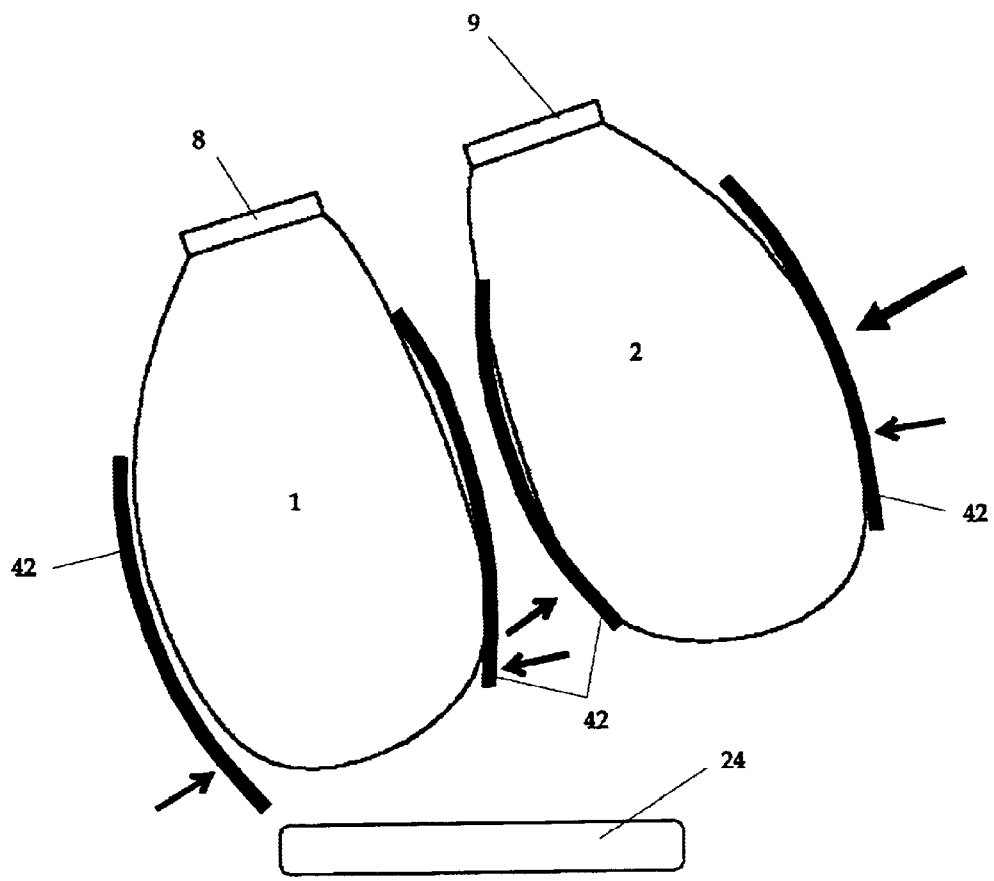
FIG. 13. View of the upper part of the cross section B–B1 in FIG. 12, where two sets of two lateral moving surfaces is outlined.

An electro-mechanic variation of the instant invention is that in which the blood pumping function is effected by a different driving mechanism as shown in FIGS. 10, 11, 12 and 13. The right blood chamber 1, is connected on the back to its respective right inlet port 8 through which it receives the blood from the right auricle. The left blood chamber 2 is connected on the back to its left inlet port 9 through which it receives the blood from the left auricle. In the front of inlet ports 8 and 9, as shown in FIGS. 11 and 13, both blood chambers are extended up to the breastbone 24, and this part of both blood chambers are placed parallel, in a somewhat oblique direction to the left.

In FIG. 10, we can see the simultaneous, joint and direct compressing action produced by two lateral moving surfaces 41, on the right lateral wall of the right blood chamber 1, and on the left lateral wall of the left blood chamber 2, moved by the driving mechanism 6. FIG. 11 is a cross-sectional view A–A1 of FIG. 10, which is at the level of inlet ports 8 and 9 of the right 1 and left 2 blood chambers. Here we can see that their front sectors, close to the breastbone 24, are placed with their inner lateral sides in a parallel position and together, and are supported by each other to receive the joint lateral compressing effect of the two lateral moving surfaces 41.

An electro-mechanic variation of said compressing mechanism is shown in FIG. 12 and FIG. 13, in which the direct compressing action is produced by one pair of lateral moving surfaces 42 for each blood chamber, each pair acting independently on the lateral walls of said blood chambers. Said moving surfaces 42 are moved by the driving mechanism 6.

Yet another variation of the instant invention consists on an arrangement comprising two outer compressing chambers, each one enclosing its respective blood chamber, said outer compressing chambers having one or more moving surfaces. Said outer compressing chambers can be separate from each other or share a common wall, said common wall becoming then a septum dividing the inner spaces of each outer compressing chamber. Each said outer compressing chamber has at least two openings; one of the openings coincides with the inlet port and another opening coincides with the outlet port through which blood comes in an out respectively. The space enclosed between each outer compressing chamber and its respective blood chamber is filled with a compressing fluid. Said compressing fluid's function is to transmit the forces exerted on the movable surfaces of the outer compressing chamber into the blood chamber which is soft and flexible. Hence, a reduction in the volume effected on the outer compressing chamber by the compressing mechanism results on a concomitant reduction in the inner volume of the blood chamber. Said compressing mechanism is driven by at least one power source, also located inside the mediastinum. Said reduction in the inner volume of each blood chamber ejects the blood contained by it. This assembly enables the independent management of systemic and pulmonary flow rates with all the advantages outlined above.

Still another variation of the instant invention consists on an arrangement comprising two outer compressing chambers. Said outer compressing chambers can be separate from each other or share a common wall, said common wall becoming then a septum dividing the inner spaces of each outer compressing chamber. Each said outer compressing chamber encloses its respective blood chamber, said outer compressing chambers being characterized by their low volume change upon changes in internal pressure occurring during use. Each said outer compressing chamber has at least three openings; one of the openings coincides with the inlet port and another opening coincides with the outlet port through which blood comes in an out respectively. The space enclosed between each outer compressing chamber and its respective blood chamber is filled with a compressing fluid. Each said outer compressing chamber has at least one opening through which compressing fluid is added or withdrawn into each outer compressing chamber. The cyclic addition and withdrawal of compressing fluid in and out of each outer compressing chamber effects the compression and expansion of the enclosed blood chambers, which are soft and flexible. The preferred compressing fluid is a gas, more preferably an inert gas. The reduction in the inner volume of each blood chamber ejects the blood contained by it. This assembly enables the independent management of systemic and pulmonary flow rates with all the advantages outlined above.

Another variation of the instant invention refers to a variation of the independently varying discharging volumes mechanism. This mechanism has been designed in order to be able to vary independently the volume ejected by each blood chamber. This variation consists on blood chambers with different volumes. For example, the right blood chamber 1 has an inner volume of 85 cc, and the left blood chamber 2 has an inner volume of 95 cc. The right blood chamber 1 ejects blood to the pulmonary circuit, which pumps against an average pressure of 50 to 25 mm of Hg. This pressure is lower than the pressure at which the left blood chamber 2 ejects to the systemic circuit, which has an average arterial pressure of 120 to 80 mm Hg. Due to the different pressures at which each of the blood chambers ejects, being the pressure of the right blood chamber 1 lower, when the variable displacement of the moving surfaces displaces a volume lower than 170 cc, for example 160 cc, the right blood chamber 1 is totally emptied and ejects 85 cc and the left blood chamber 2 ejects only 75 cc. When there is a compressing displacement of 170 cc, both blood chambers eject 85 cc each. When there is a compressing displacement of 180 cc, the left blood chamber 2 ejects 10 cc more than the right blood chamber.

Summarizing:

| Moving surface Displacement | RBS Ejection | LBS Ejection |
| --- | --- | --- |
| 160 cc. | 85 cc. | 75 cc. |
| 170 cc. | 85 cc. | 85 cc. |
| 180 cc. | 85 cc. | 95 cc. |

This improvement of the independently varying discharging volumes is also applied to the variant of the instant invention effecting the blood pumping using a direct compressing action of the blood chambers as shown in FIG. 10 and FIG. 11 where the pressure is produced jointly.by the lateral moving surfaces 41. It first empties the right blood chamber 1, which ejects against a lower pulmonary circuit pressure and the lateral moving surfaces displacement is regulated to vary the blood flow in each circuit according to the physiological needs.

In the variant in which each blood chamber has two separate lateral moving surfaces 42, the displacement of each pair of them is adjusted in order to independently handle the volumes ejected.

Those skilled in the art will recognize, or be able to ascertain using no more than routine experimentation, many equivalents to the specific embodiments of the invention specifically described herein. Such equivalents are intended to be encompassed in the scope of the following claims.

What is claimed is:

1. An artificial heart for insertion in a living being subjected to surgery in which the lower sector of the aorta artery and main pulmonary artery have been surgically liberated, and then transposed with respect to their native antero-posterior position comprising:

one right blood chamber, said right blood chamber having one right inlet port for blood to enter, said right inlet port having means for attachment to the right atrium, said right blood chamber including one posterior outlet port for blood to exit said right blood chamber, said posterior outlet port having means for attachment to the main pulmonary artery, one left blood chamber, said left blood chamber having one left inlet port for blood to enter, said left inlet port having means for attachment to the left atrium, said left blood chamber including one anterior outlet port for blood to exit said left blood chamber, said anterior outlet port having means for attachment to the aorta artery, wherein the spatial arrangement between said right and left blood chambers being such that a part of the right blood chamber is posterior to the corresponding part of the left blood chamber, in such a way that their outlet ports are placed in a transposed position with regard to the normal anatomy of the native heart, and means for squeezing and directing blood into and out of said right and left blood chambers.

2. An artificial heart as defined in claim 1, wherein both said blood chambers are soft and flexible.

3. An artificial heart as defined in claim 1, wherein each of the innermost walls of both multiple-walled blood chambers are made of pericardium single piece.

4. An artificial heart as defined in claim 1 wherein said blood chambers have expanded capacity between 20 mL and 120 mL each, preferably between 40 mL and 100 mL each.

* * * * *